(12) United States Patent
Ashman

(10) Patent No.: US 8,241,297 B2
(45) Date of Patent: Aug. 14, 2012

(54) SURGICAL DRILL GUIDE FOR SHAPE MEMORY CLAMPS

(75) Inventor: Richard B. Ashman, New Orleans, LA (US)

(73) Assignee: Intelifuse, Inc., Metairie, LA (US)

( * ) Notice: Subject to any disclaimer, the term of this patent is extended or adjusted under 35 U.S.C. 154(b) by 297 days.

(21) Appl. No.: 12/595,407

(22) PCT Filed: Apr. 10, 2008

(86) PCT No.: PCT/US2008/059892
§ 371 (c)(1),
(2), (4) Date: Feb. 22, 2010

(87) PCT Pub. No.: WO2008/124818
PCT Pub. Date: Oct. 16, 2008

(65) Prior Publication Data
US 2010/0145351 A1  Jun. 10, 2010

Related U.S. Application Data

(60) Provisional application No. 60/910,853, filed on Apr. 10, 2007.

(51) Int. Cl.
| | |
|---|---|
| *A61B 17/58* | (2006.01) |
| *A61B 17/60* | (2006.01) |
| *A61F 2/00* | (2006.01) |
| *B23B 49/00* | (2006.01) |
| *B23Q 17/22* | (2006.01) |
| *B27G 23/00* | (2006.01) |
| *G01D 21/00* | (2006.01) |
| *B65D 81/24* | (2006.01) |

(52) U.S. Cl. .............. 606/96; 33/640; 206/206
(58) Field of Classification Search ............ 606/96, 606/87, 98; 408/115 B, 202, 241 G; 30/286; 422/547; 206/206, 339; 33/640, 641
See application file for complete search history.

(56) References Cited

U.S. PATENT DOCUMENTS

| | | | | |
|---|---|---|---|---|
| 3,148,562 | A | * | 9/1964 | Moss .............................. 408/75 |
| 4,705,436 | A | * | 11/1987 | Robertson ................... 408/72 R |
| 4,834,080 | A | * | 5/1989 | Brown ............................. 606/96 |
| 5,053,037 | A | | 10/1991 | Lackey |

(Continued)

OTHER PUBLICATIONS

International Search Report and The Written Opinion of the International Searching Authority, International Application No. PCT/US2008-059892, filed Apr. 10, 2008.

*Primary Examiner* — Kevin T Truong
*Assistant Examiner* — David Bates
(74) *Attorney, Agent, or Firm* — St. Onge Steward Johnston & Reens LLC

(57) ABSTRACT

A surgical drill guide for guiding a drill bit and limiting the depth of holes drilled by is disclosed. In some embodiments the surgical drill guide includes the following: a body including a drill bit entry side and a tissue contact side opposite the drill bit entry side, the drill bit entry side having first and second surfaces that are offset from one another, the tissue contact side including a tissue contact surface that is defined by one or more tissue contact points; drill bit guide holes extending from the drill bit entry side of the first and second surfaces to the tissue contact side of the body; and implant storage holes defined in one of the plurality of sides of the body for storing shape memory implants during shipment of the system, the implant storage holes being spaced a distance commensurate to dimensions of the shape memory implant.

17 Claims, 5 Drawing Sheets

U.S. PATENT DOCUMENTS

| | | |
|---|---|---|
| 5,306,278 A * | 4/1994 | Dahl et al. .................. 606/96 |
| 5,634,927 A * | 6/1997 | Houston et al. ............. 606/96 |
| 5,769,856 A * | 6/1998 | Dong et al. .................. 606/96 |
| 5,810,830 A | 9/1998 | Noble et al. |
| 5,888,034 A | 3/1999 | Greenberg |
| 5,954,769 A | 9/1999 | Rosenlicht |
| 6,127,597 A | 10/2000 | Beyar et al. |
| RE37,425 E * | 10/2001 | Izumitami ................... 351/110 |
| 2004/0153087 A1* | 8/2004 | Sanford et al. .............. 606/88 |
| 2008/0114370 A1* | 5/2008 | Schoenefeld ................ 606/96 |

* cited by examiner

SURGICAL DRILL GUIDE FOR SHAPE MEMORY CLAMPS

CROSS REFERENCE TO RELATED APPLICATION(S)

This application claims the benefit of U.S. Provisional Application No. 60/910,853, filed Apr. 10, 2007, which is incorporated by reference as if disclosed herein in its entirety.

BACKGROUND

When placing a surgical implant in the tissue of a patient, holes must be drilled at precise locations and depths in the tissue to ensure proper placement of the implant. The placement of surgical implants, e.g., shaped as two prong staples, four prong staples, as well as multi-holed plates with screw fixation, requires that holes be predrilled in tissue at precise locations. Pre-drilling of holes can be centered on the staple prongs or plate holes, or can be offset to provide some amount of pre-loading of the implant. For example, holes may be predrilled slightly further apart than the implants prongs to provide compression across a fracture site. Conversely, holes can be predrilled closer together than the implant prongs to create distraction loading. Hole depth must also be controlled. Holes can be planned to pierce one cortex of a bone, or provide implant fixation bi-cortically.

A class of surgical implant is made from a shape memory material such as a nickel alloy known as nitinol. Material such as nitinol or exhibiting similar characteristics as nitinol can be formed into implants, which can be made to transform their shape at some specific transformation temperature. Shape memory implants can have transformation temperatures either below body temperature or slightly above body temperature.

When the transformation temperature is designed to be below that of body temperature, the implant must be held in the implantable shape during storage. Prior to use, the implant is cooled below its transformation temperature. Once it is implanted, body temperature warms the implant above its transformation temperature. Typically, a block of plastic with precise holes is included with the implant to hold it in its implantable form.

For implants where the transformation temperature of the shape memory material is designed to be at a temperature slightly above body temperature, the implant must also be shipped and stored in a plastic holder or block. Again, holes in the plastic holder keep the implant from transforming into its higher temperature shape.

Because of the different sizes and shapes of implants available, an adjustable drill guide is used to guide the drilling. However, because two and four pronged implants are available, at least two different drill guides are necessary. Furthermore, because the prongs or legs of the implants are of different length, drill bits of specific lengths must be provided to drill the holes to a specified depth.

SUMMARY

A surgical drill guide for guiding a drill bit and limiting the depth of holes drilled by the drill bit according to dimensions of a shape memory implant to be inserted into the holes is disclosed. In some embodiments, the surgical drill guide includes the following: a body having a plurality of sides including a drill bit entry side and a tissue contact side opposite the drill bit entry side, the drill bit entry side having first and second surfaces that are offset from one another thereby defining a first thickness between the first surface of the drill bit entry side and the tissue contact side and a second thickness between the second surface of the drill bit entry side and the tissue contact side, the tissue contact side including a tissue contact surface that is defined by one or more tissue contact points; drill bit guide holes extending from and through the drill bit entry side of the first and second surfaces to and through the tissue contact side of the body; and implant storage holes defined in at least one of the plurality of sides of the body for storing shape memory implants during shipment of the system, the implant storage holes being spaced a distance substantially equivalent to dimensions of the shape memory implant.

Systems for guiding a drill bit and limiting the depth of holes drilled by the drill bit according to dimensions of a shape memory implant to be inserted into the holes are disclosed. In some embodiments, the system includes the following: a body having a plurality of sides including a drill bit entry side and a tissue contact side opposite the drill bit entry side, the drill bit entry side having first and second surfaces that are offset from one another thereby defining a first thickness between the first surface of the drill bit entry side and the tissue contact side and a second thickness between the second surface of the drill bit entry side and the tissue contact side, the tissue contact side including a tissue contact surface that is defined by one or more tissue contact points; drill bit guide holes extending from and through the drill bit entry side of the first and second surfaces to and through the tissue contact side of the body, the drill bit guide holes being laterally offset according to dimensions of the shape memory implant; a drill bit including a collar or offset shank for limiting a depth the drill bit can be extended through the drill bit guide holes and into a patient's tissue; and implant storage holes defined in at least one of the plurality of sides of the body for storing shape memory implants, the implant storage holes being spaced a distance substantially equivalent to dimensions of the shape memory implant.

A surgical drill guide for guiding a drill bit and limiting the depth of holes drilled by the drill bit according to dimensions of a shape memory implant to be inserted into the holes is disclosed. In some embodiments, the surgical drill guide includes the following: a body having a plurality of sides including a drill bit entry side and a tissue contact side opposite the drill bit entry side, the drill bit entry side having first and second surfaces that are offset from one another thereby defining a first thickness between the first surface of the drill bit entry side and the tissue contact side and a second thickness between the second surface of the drill bit entry side and the tissue contact side, the tissue contact side including a tissue contact surface that is defined by one or more tissue contact points; drill bit guide holes extending from and through the drill bit entry side of the first and second surfaces to and through the tissue contact side of the body; implant storage holes defined in at least one of the plurality of sides of the body for storing shape memory implants during shipment of the system, the implant storage holes being spaced a distance substantially equivalent to dimensions of the shape memory implant; a removable handle; and one or more handle attachment holes defined in at least one of the plurality of sides of the body for detachably connecting the handle with the body.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Generally, the disclosed subject matter relates to systems and guides for directing a surgical drill and drill bit and limiting the depth of holes drilled by the drill bit according to dimensions of a shape memory implant to be inserted into the holes.

Figure 1:
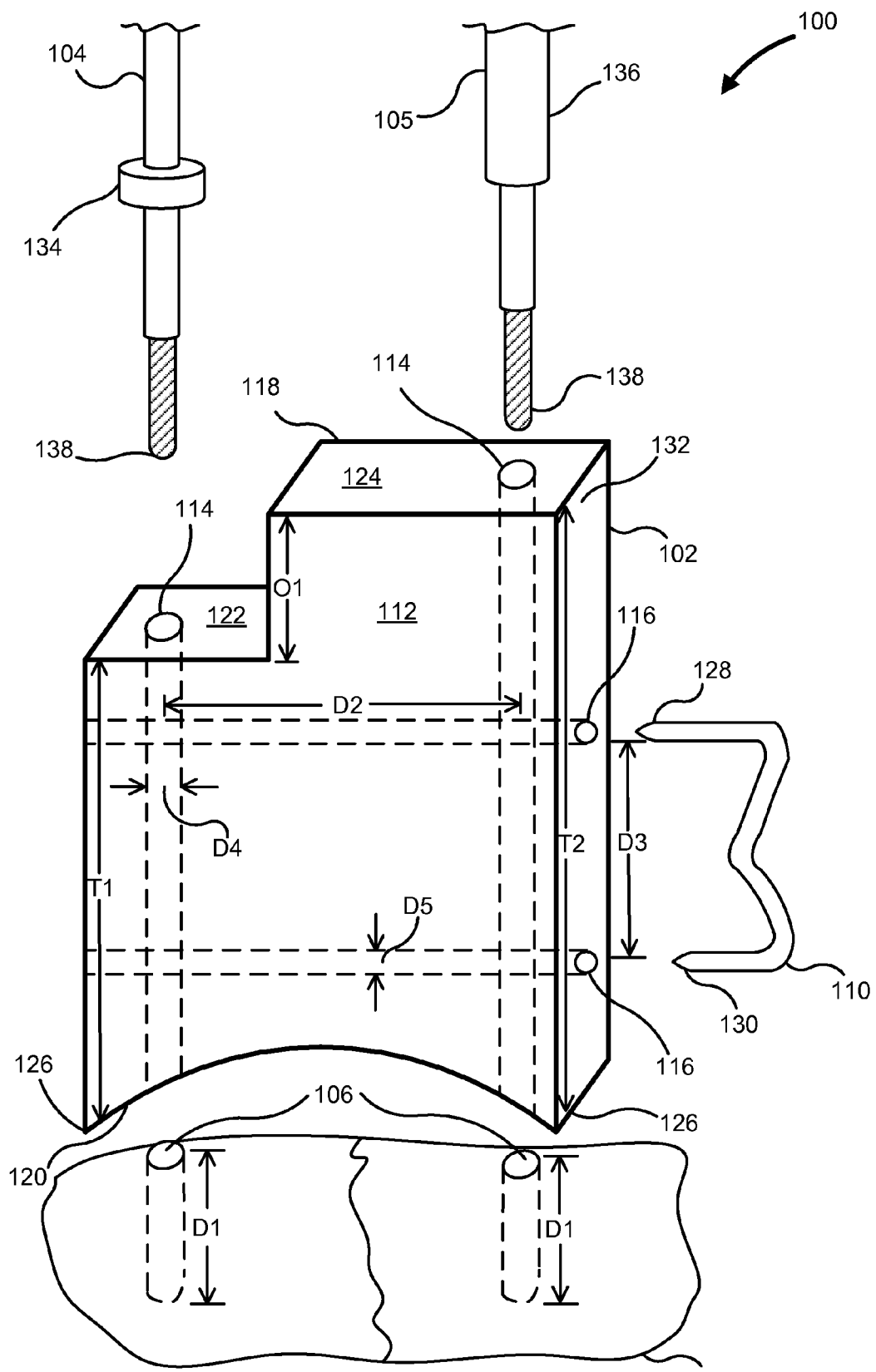
FIG. 1 is a front isometric view of a drill guide and drill guide system according to some embodiments of the disclosed subject matter.
Figure 2:
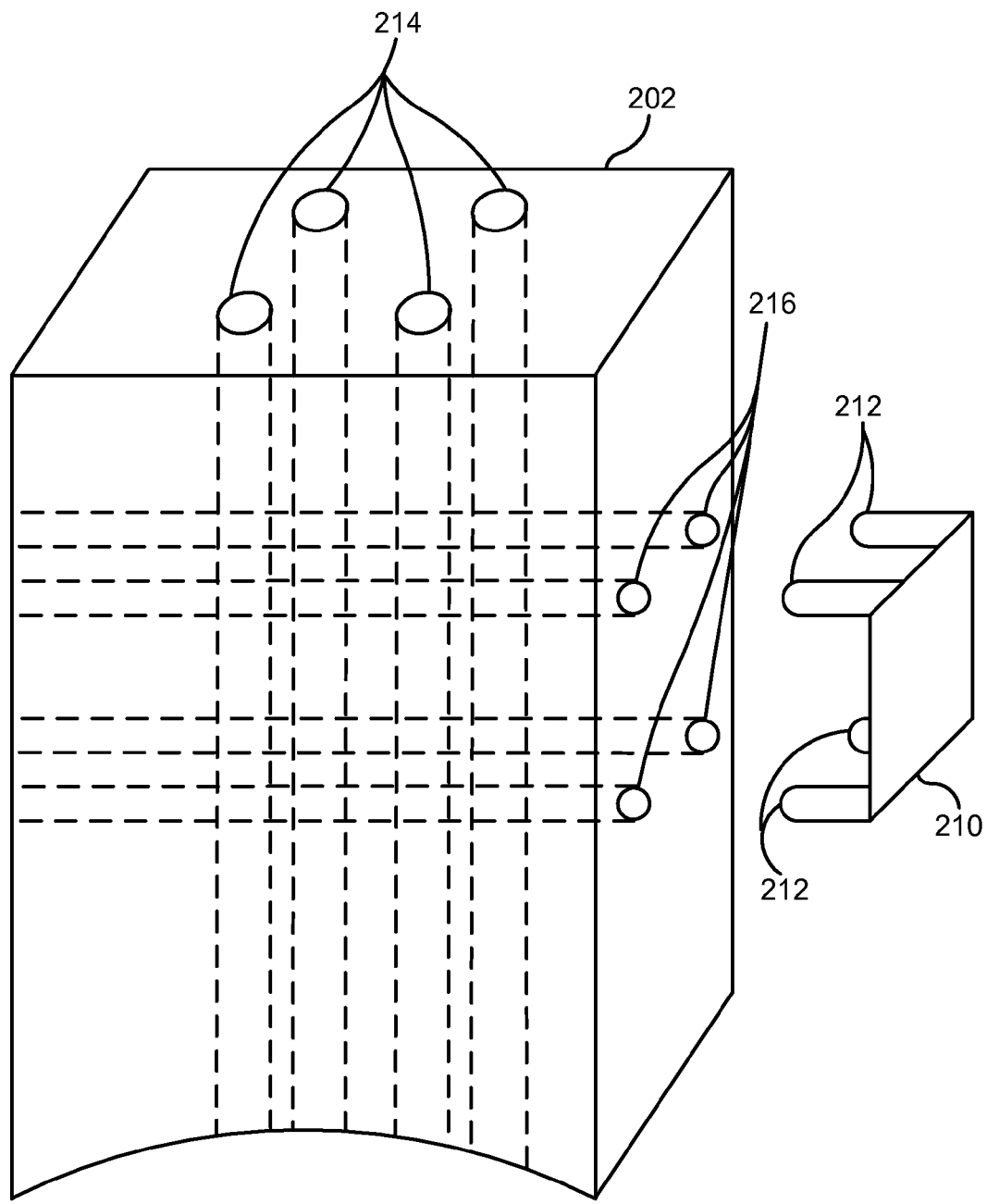
FIG. 2 is a front isometric view of a drill guide for two and four pronged implants according to some embodiments of the disclosed subject matter.

Referring now to FIGS. 1 and 2, some embodiments of the disclosed subject matter include a system 100 and surgical drill guide 102 for guiding drill bits 104, 105 and limiting the depth D1 of holes 106 drilled by the drill bit into tissue 108 of a patient according to dimensions of a shape memory implant 110 to be inserted into the holes. Surgical drill guide 102 is defined by a body 112, which includes drill bit guide holes 114 for guiding drill bit 102, and implant storage holes 116 for storing shape memory implant 110.

Body 112 includes a plurality of sides, including a drill bit entry side 118 and a tissue contact side 120 opposite the drill bit entry side. Body 112 is typically fabricated from a molded or machined material. Typical materials include plastics, stainless steel, steel alloys, and other materials that do not chemically react with either memory shape implant 110 or drill bits 104 and 105. Drill bit entry side 118 includes first and second surfaces 122, 124, respectively, which are offset by a distance O1 from one another. Offset O1 between first surface 122 and second surfaces 124 defines a stepped configuration having a first thickness T1 between the first surface of drill bit entry side 118 and tissue contact side 120 and a second thickness T2 between the second surface of the drill bit entry side and the tissue contact side. Tissue contact side 120 includes a tissue contact surface (not shown) that is defined by one or more tissue contact points 126. As discussed further below, tissue contact points 126 can be configured so as to contact specific points of tissue 108.

Drill bit guide holes 114 extend from and through drill bit entry side 118 to and through tissue contact side 120. Drill bit guide holes 114 are laterally offset or positioned away from one another by a distance D2 that is substantially equivalent to a distance D3 between prongs 128, 130 of shape memory implant 110. Drill bit guide holes 114 typically have a diameter D4 that is selected to allow drill bits 104, 105 to slip and rotate freely within the holes.

Implant storage holes 116 are defined in at least one of the plurality of sides of body 112, e.g., a side surface 132, and are used to store shape memory implant 110 during shipment of system 100. Implant storage holes 116 are spaced a distance D3, which is substantially equivalent to the distance between prongs 128, 130 of shape memory implant 110. Implant storage holes 116 are positioned so as to define openings that are offset from the openings defined by drill bit guide holes 114.

Implant storage holes 116 have a diameter D5 sufficient to allow shape memory implant 110 to be inserted and stored during shipping.

Still referring to FIG. 1, drill bits 104, 105 can be used in conjunction with the stepped configuration of drill bit entry side 118 of surgical drill guide 102 to form system 100 for guiding the drill bits and limiting the depth D1 of holes 106 drilled by the drill bit into tissue 108 of a patient according to dimensions of shape memory implant 110, which will be inserted into the holes. In some embodiments, drill bit 104 includes a collar 134 or drill bit 105 includes an offset shank 136, both of which are designed to limit a depth that the drill bits can be extended through drill bit guide holes 114 and into tissue 108 of a patient's. The stepped configuration of drill bit entry side 118 of surgical drill guide 102 and collar 134 or offset shank 136 of drill bits 104, 105, respectively, limits the length of drill bits that extends from drill bit guide holes 114 to a specific distance, thus controlling depth D1 of holes 106 that are drilled into tissue 108. As one skilled in the art will appreciate, depth D1 can be controlled by adjusting offset O1, adjusting the position of collar 134 or offset shank 136 on drill bits 104, 105, respectively, and adjusting the length of the drilling ends 138 of the drill bits.

In some embodiments, system 100 can also include shape memory implant 110, which is sized to fit within implant storage holes 116. If fabricated from a shape memory material such as nitinol, shape memory implant 110 must be held in its "opened" or implantable shape during shipping and storage. The properties of nitinol allow the material to exist in two stable phases. The lower temperature phase is referred to as the martensitic phase, due to its metallic structure being composed primarily of martensite. The higher temperature phase is referred to as the austenitic phase. Nitinol is an alloy composed primarily of nickel and titanium. By varying the percentage of nickel and titanium, different transition temperatures can be achieved. Transformation temperatures can be either below that of body temperature or slightly greater than body temperature. As discussed above, implant storage holes 116 are sized and spaced to hold shape memory implant 110 in its implantable shape.

Referring now to FIG. 2, in some embodiments, a body 202 is configured to accommodate a shape memory implant 210, which has a plurality of prongs 212, e.g., four prongs, etc. Body 200 includes a plurality of drill bit guide holes 214 and a plurality of implant storage holes 216.

Figure 3A:
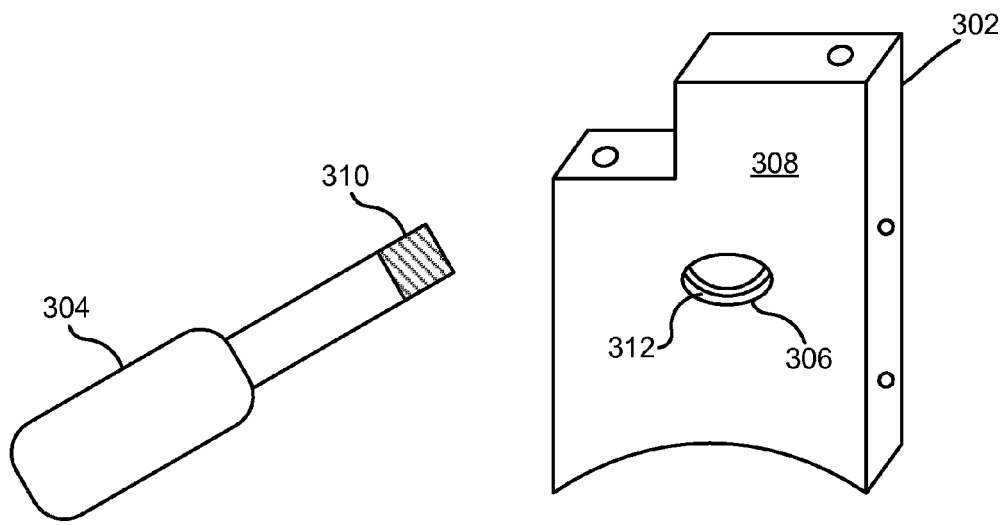
FIGS. 3A-3C are front isometric views of handle designs according to some embodiments of the disclosed subject matter.
Figure 3B:
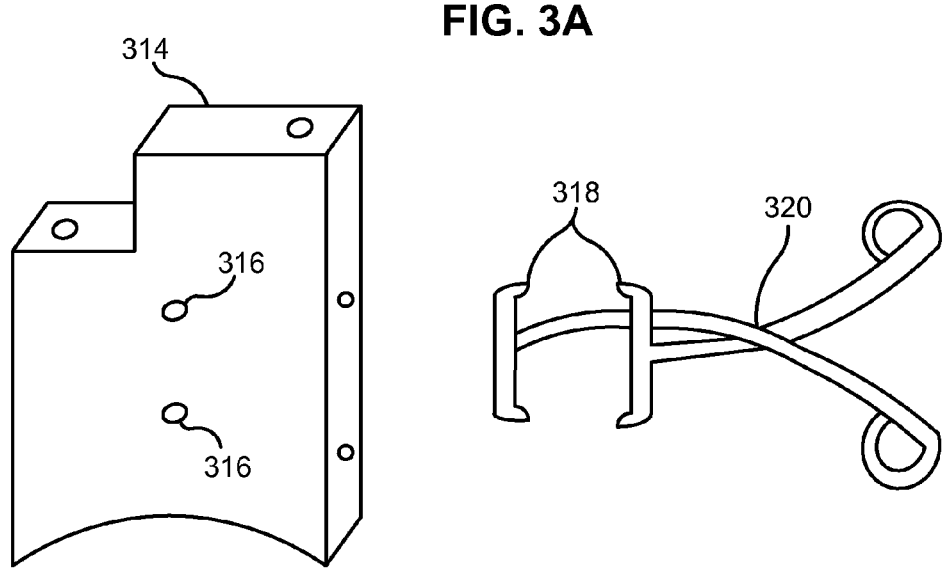
Figure 3C:
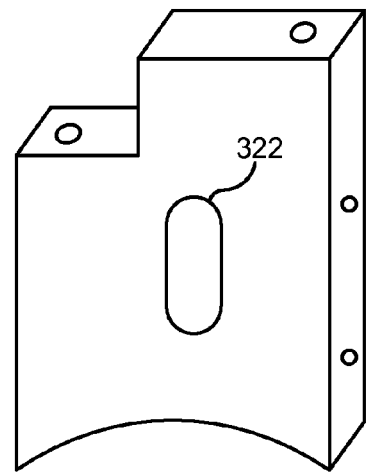

Referring now to FIGS. 3A-3C, some embodiments of the disclosed subject matter allow attachment of a removable handle to the body for manipulating the drill guide during use in surgery. As shown in FIG. 3A, some embodiments include a body 302 having a removable handle 304 and one or more handle attachment holes 306 defined in a side 308 of the body for detachably connecting the handle with the body. Removable handle 304 can be shaped similar to a screwdriver and include a threaded end 310 that mates with threads 312 defined in attachment hole 306. Removable handle 304 is typically formed from a resterilizable material, but can also be disposed of after a single use. Prior to use, removable handle 304 is screwed into attachment hole 306.

Referring now to FIGS. 3B and 3C, some embodiments include a body 314 having a plurality of holes 316 that match the jaws 318 of an instrument 320. Instrument 320 is used for manipulating the drill guide during use in surgery. Alternatively, as shown in FIG. 3C, holes 316 can be replaced with an oblong hole 322 or milled grooves (not shown) that are configured to mate with a holder instrument (also not shown).

Figure 4:
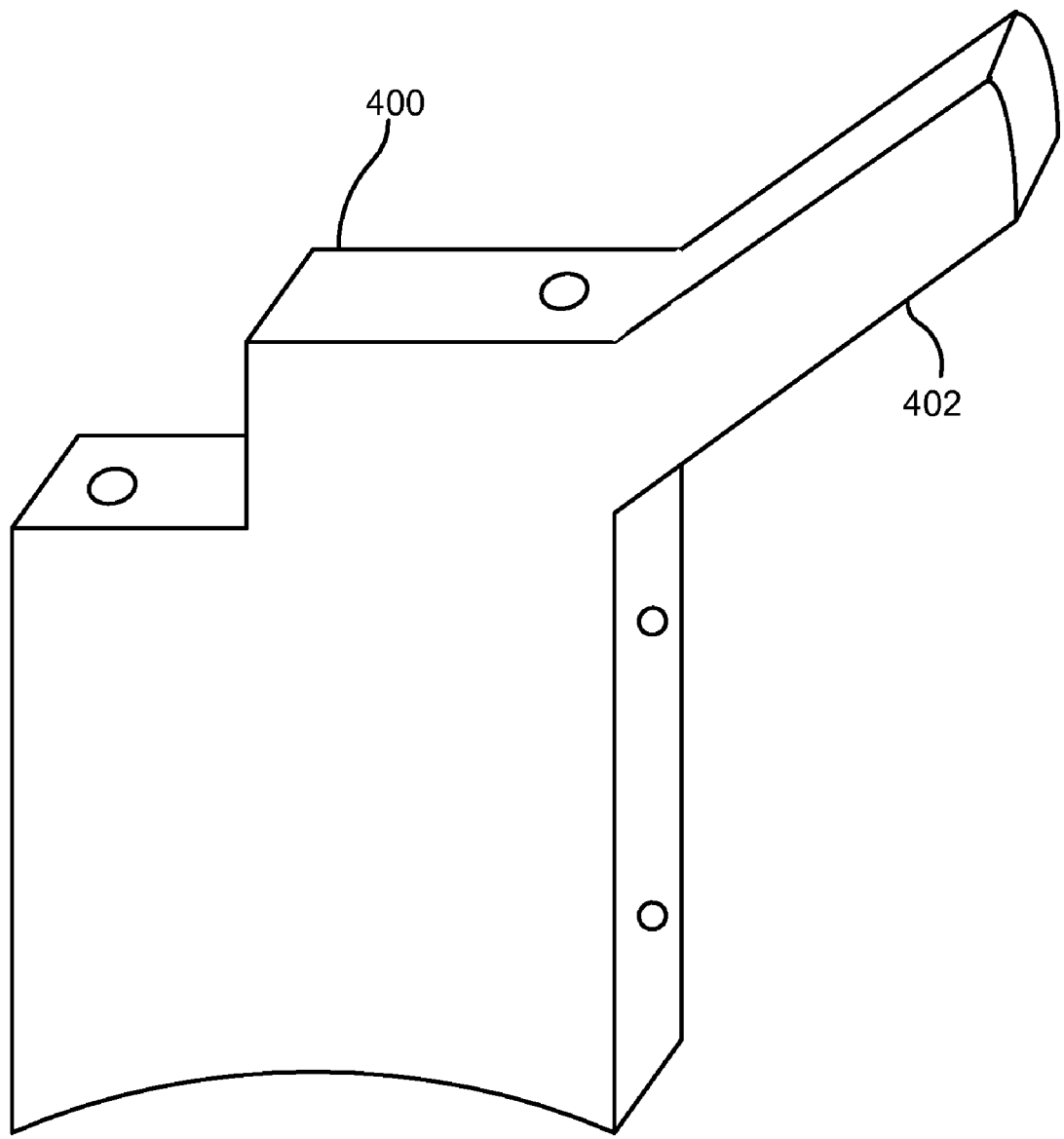
FIG. 4 is a front isometric view of a handle design according to some embodiments of the disclosed subject matter.

Referring now to FIG. 4, some embodiments include a body 400 having an integral handle portion 402 extending therefrom. Handle portion 402 is typically, but not always, formed from the same material used to fabricate body 400 and is used for manipulating the drill guide during use in surgery.

Figure 5A:
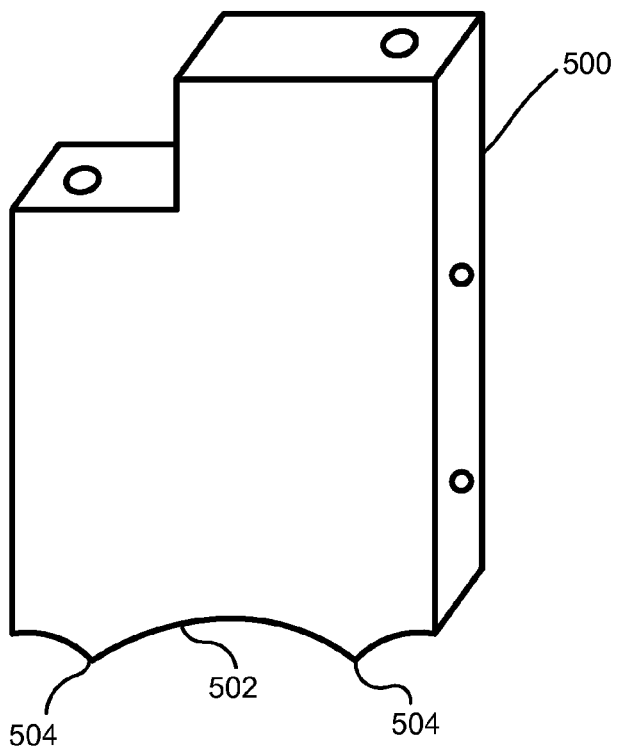
FIGS. 5A and 5B are front isometric views of tissue contact end configurations according to some embodiments of the disclosed subject matter.
Figure 5B:
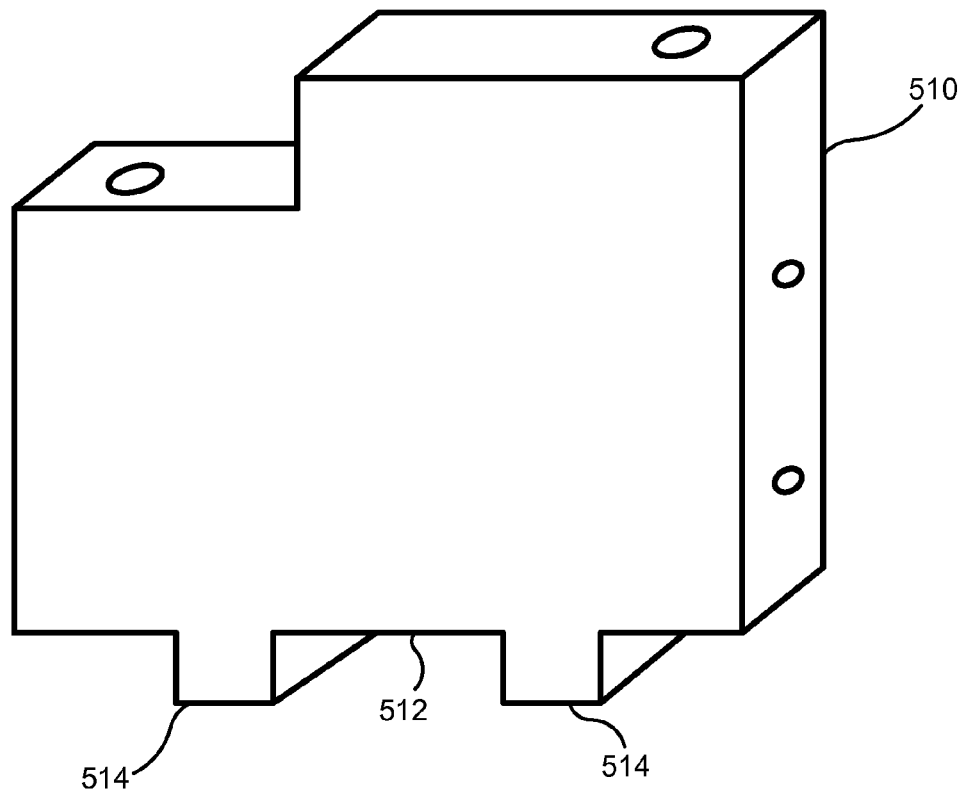

Referring now to FIGS. 5A and 5B, some embodiments include a body having one or more tissue contact points that are configured to match a topography of tissue (not shown) of a particular patient, e.g., an irregular bone shape, etc. As shown in FIG. 5A, in some embodiments, body 500 includes a tissue contact end 502 that has pointed portions 504 for contacting the tissue at specific points. This can be particularly necessary when the drill guide is used on irregularly shaped bone. As shown in FIG. 5B, in some embodiments, body 510 includes a tissue contact end 512 that has raised portions 514 for contacting the tissue at specific points. Other embodiments can be devised according to the particular topography of a patient's tissue.

The guides and systems according to the disclosed subject matter provide an improved device for drilling holes during surgical procedures. Holes formed through the body of the device correspond to the pattern and location where holes are to be drilled into the tissue during surgery. The thickness of the device at the location of each hole, when combined with a stepped or collared drill bit, limits the drilled hole to a specific depth. Other holes formed in the body of the device are used to hold the shape of shape memory alloy implants during sterilization, shipping, and storage.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A surgical drill guide system for guiding a drill bit and limiting the depth of holes drilled by the drill bit according to dimensions of a shape memory implant to be inserted into the holes, said surgical drill guide comprising:
    a body having a plurality of sides including a drill bit entry side and a tissue contact side opposite said drill bit entry side, said drill bit entry side having first and second surfaces that are offset from one another thereby defining a first thickness between said first surface of said drill bit entry side and said tissue contact side and a second thickness between said second surface of said drill bit entry side and said tissue contact side, said tissue contact side including a tissue contact surface that is defined by one or more tissue contact points;
    drill bit guide holes extending from and through said drill bit entry side of said first and second surfaces to and through said tissue contact side of said body; and
    a shape memory implant that is sized to fit within implant storage holes defined in at least one of said plurality of sides of said body during shipment of said system, said implant storage holes being spaced a distance substantially equivalent to dimensions of the shape memory implant;
    wherein the distance between the drill bit guide holes is substantially equivalent to the distance between the implant storage holes.

2. The surgical drill guide according to claim 1, further comprising a drill bit including a collar or offset shank for limiting a depth that said drill bit can be extended through said drill bit guide holes and into a patient's tissue.

3. The surgical drill guide according to claim 1, further comprising:
    a removable handle; and
    one or more handle attachment holes defined in at least one of said plurality of sides of said body for detachably connecting said handle with said body.

4. The surgical drill guide according to claim 1, wherein said body includes an integral handle portion extending from at least one of said plurality of sides.

5. The surgical drill guide according to claim 1, wherein said one or more tissue contact points are configured to match a topography of tissue of a patient.

6. The surgical drill guide according to claim 5, wherein said one or more tissue contact points are configured contact an irregular bone shape of a patient.

7. The surgical drill guide according to claim 1, wherein said drill bit guide holes are laterally offset according to dimensions of said shape memory implant.

8. A surgical drill guide system for guiding a drill bit and limiting the depth of holes drilled by the drill bit according to dimensions of a shape memory implant to be inserted into the holes, said system comprising:
    a body having a plurality of sides including a drill bit entry side and a tissue contact side opposite said drill bit entry side, said drill bit entry side having first and second surfaces that are offset from one another thereby defining a first thickness between said first surface of said drill bit entry side and said tissue contact side and a second thickness between said second surface of said drill bit entry side and said tissue contact side, said tissue contact side including a tissue contact surface that is defined by one or more tissue contact points;
    drill bit guide holes extending from and through said drill bit entry side of said first and second surfaces to and through said tissue contact side of said body, said drill bit guide holes being laterally offset according to dimensions of the shape memory implant; a drill bit including a collar or offset shank for limiting a depth said drill bit can be extended through said drill bit guide holes and into a patient's tissue; and
    a shape memory implant that is sized to fit within implant storage holes defined in at least one of said plurality of sides of said body, said implant storage holes being spaced a distance substantially equivalent to dimensions of the shape memory implant;
    wherein the distance between the drill bit guide holes is substantially equivalent to the distance between the implant storage holes.

9. The surgical drill guide system according to claim 8, further comprising:
    a removable handle; and
    one or more handle attachment holes defined in at least one of said plurality of sides of said body for detachably connecting said handle with said body.

10. The surgical drill guide system according to claim 8, wherein said body includes an integral handle portion extending from at least one of said plurality of sides.

11. The surgical drill guide system according to claim 8, wherein said one or more tissue contact points are configured to match a topography of tissue of a patient.

12. The surgical drill guide according to claim 11, wherein said one or more tissue contact points are configured contact an irregular bone shape of a patient.

13. A surgical drill guide system for guiding a drill bit and limiting the depth of holes drilled by the drill bit according to dimensions of a shape memory implant to be inserted into the holes, said surgical drill guide comprising:
    a body having a plurality of sides including a drill bit entry side and a tissue contact side opposite said drill bit entry side, said drill bit entry side having first and second surfaces that are offset from one another thereby defining a first thickness between said first surface of said drill bit entry side and said tissue contact side and a second thickness between said second surface of said drill bit entry side and said tissue contact side, said tissue contact side including a tissue contact surface that is defined by one or more tissue contact points;

drill bit guide holes extending from and through said drill bit entry side of said first and second surfaces to and through said tissue contact side of said body;

a shape memory implant that is sized to fit within implant storage holes defined in at least one of said plurality of sides of said body during shipment of said system, said implant storage holes. being spaced a distance substantially equivalent to dimensions of the shape memory implant;

a removable handle;

one or more handle attachment holes defined in at least one of said plurality of sides of said body for detachably connecting said handle with said body; and, wherein the distance between the drill bit guide holes is substantially equivalent to the distance between the implant storage holes.

14. The surgical drill guide according to claim 13, further comprising a drill bit including a collar or offset shank for limiting a depth that said drill bit can be extended through said drill bit guide holes and into a patient's tissue.

15. The surgical drill guide according to claim 13, wherein said one or more tissue contact points are configured to match a topography of tissue of a patient.

16. The surgical drill guide according to claim 15, wherein said one or more tissue contact points are configured contact an irregular bone shape of a patient.

17. The surgical drill guide according to claim 13, wherein said drill bit guide holes are laterally offset according to dimensions of said shape memory implant.

* * * * *